US004001746B2

United States Statutory Invention Registration [19]

[11] Reg. Number: H1746

[45] Published: Aug. 4, 1998

Carrier et al.

[54] ABSORBENT ARTICLE HAVING ANTI-WICKING CRIMP SEAL

[75] Inventors: Michael Edward Carrier; Robert E. Lee Marshall, III; Richard George Coe, all of Cincinnati, Ohio

[73] Assignee: The Procter & Gamble Company, Cincinnati, Ohio

[21] Appl. No.: 788,073

[22] Filed: Jan. 22, 1997

Related U.S. Application Data

[63] Continuation of Ser. No. 291,314, Aug. 16, 1994, abandoned, which is a continuation of Ser. No. 65,876, May 21, 1993, abandoned.

[51] Int. Cl.[6] ..... A61F 13/20

[52] U.S. Cl. ..... 604/385.1

*Primary Examiner*—Charles T. Jordan
*Assistant Examiner*—Meena Chelliah
*Attorney, Agent, or Firm*—Jeffrey V. Bamber; Steven W. Miller; Jacobus C. Rasser

[57] ABSTRACT

An absorbent article is disclosed for absorbing liquids, including body fluids such as menstrual discharges or urine. The absorbent article has a liquid impermeable backsheet on which is disposed an absorbent core, and first and second liquid permeable topsheet layers. The edge of the absorbent core defines a perimeter, and the first and second topsheet layers and the backsheet each extend laterally beyond the perimeter to define a continuous border segment surrounding the absorbent core. A liquid impermeable seal is formed in the border segment which surrounds the perimeter for preventing lateral migration of liquid from the absorbent core beyond the seal. The seal is formed to extend from an outer surface of the first topsheet layer to an outer surface of the backsheet, for establishing a capillary gradient in the second topsheet layer, thereby inhibiting wicking of fluid therethrough.

1 Claim, 2 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

ABSORBENT ARTICLE HAVING ANTI-WICKING CRIMP SEAL

This is a continuation of application Ser. No. 08/291,314, filed on Aug. 16, 1994, abandoned which is a continuation of application Ser. No. 08/065,876, filed on May 21, 1993 abandoned.

BACKGROUND OF THE INVENTION

1. Technical Field

The present invention relates generally to disposable absorbent articles and, more particularly, to the incorporation of an anti-wicking crimp seal into the peripheral border of a catamenial pad.

2. Background Art

Disposable absorbent articles are commercially available in a wide variety of configurations for the specific purpose of absorbing and retaining discharged body fluids. For example, disposable diapers and incontinent briefs are intended to absorb and contain urine and feces, bandages are intended to absorb and contain blood and other body exudates while catamenial pads are intended to absorb and retain menstrual fluids and other vaginal discharges. Regardless of the specific application, each absorbent article is intended to isolate the discharged fluids for preventing the undergarments, clothing, bedding etc. surrounding the disposable article from becoming soiled.

As is known, the basic structure for most disposable absorbent articles includes an absorbent core that is encased between a liquid permeable topsheet layer and a liquid impervious backsheet. The absorbent core generally incorporates a number of Absorbent Gelling Material (AGM) particles. However, apertured film topsheet layers known in the art have generally failed to adequately retain the AGM particles, either before or after they have absorbed liquids. It is therefore desirable to provide an improved topsheet layer for more effectively retaining the AGM particles within the absorbent article.

In addition, it is common for the topsheet layer to be affixed to the backsheet in a manner defining a continuous and relatively thin border segment which surrounds the perimeter of the thicker absorbent core. Ideally, the disposable article must exhibit good strikethrough and rewet characteristics for permitting the discharged fluid to rapidly penetrate the topsheet layer while preventing subsequent flow back through the topsheet layer. Moreover, the liquid impervious backsheet should isolate the fluid retained in the absorbent core from the wearer's undergarments or clothing. As will be appreciated, numerous variations to the above-noted structure are known in the art for improving a particular functional or comfort characteristic of the disposable absorbent article.

Due to the rapid capillary-type action associated with the strikethrough characteristics of the liquid permeable topsheet layer, the potential exists for lateral migration (i.e., "wicking") of the discharged fluid from the absorbent core toward the peripheral edge of the absorbent article. Such wicking is undesirable in that it may cause soiling of the wearer's undergarments and/or clothing in the vicinity surrounding the absorbent article. In an attempt to prevent such lateral migration of discharged fluids, it is known to form a liquid impervious "seam" in the border segment of the disposable absorbent article. For example, commonly owned U.S. Pat. No. 4,321,924 issued to Ahr discloses incorporation of a pair of continuous seams into a channelled border segment of a catamenial pad which act as barriers against edge leakage. Thus, while such conventional products perform well for their intended purpose, a continuing need exists to develop improvements in the structure, method of manufacture, and cost of bordered disposable absorbent articles.

It is therefore an object of the present invention to provide a disposable absorbent article having an improved mechanism for preventing wicking of fluid from an absorbent core toward the edges of a border segment surrounding the absorbent core.

It is another object of the present invention to provide a second liquid permeable topsheet layer in the disposable absorbent article for improved containment of the absorbent fibers and/or absorbent gelling material particles within the absorbent core. Formation of an anti-wicking seal between the first topsheet layer, the second topsheet layer and the backsheet in the border segment of the disposable article is effective in inhibiting lateral migration of fluids from the absorbent core.

SUMMARY OF THE INVENTION

According to the present invention, a disposable absorbent article is provided having an absorbent core, a liquid impermeable backsheet, a first liquid permeable topsheet layer and a second liquid permeable topsheet layer. The absorbent core is disposed between the backsheet and the second topsheet layer, and the second topsheet layer is disposed between the absorbent core and the first topsheet layer. Each of the first and second topsheet layers and the backsheet extend laterally beyond the perimeter of the absorbent core to define a continuous border segment surrounding the absorbent core. A liquid impermeable seal surrounds at least a portion of the perimeter of the absorbent core and is formed in the border segment to extend between the first and second topsheet layers and the backsheet. Moreover, the seal extends from an outer or top surface of the first topsheet layer to an outer or lower surface of the backsheet layer, and is adapted to prevent lateral migration of fluid from within the perimeter of the absorbent core beyond the seal.

These and various other objects, advantages and features of the present invention will become apparent from the following description and claims, when considered in conjunction with the appended drawings.

DETAILED DESCRIPTION OF THE PREFERRED EMBODIMENTS

The following description of the preferred embodiments is merely exemplary in nature, and is in no way intended to limit the invention, its application or uses.

With reference to the drawings, a preferred embodiment of the present invention is shown incorporated into a disposable absorbent article, and in particular, a catamenial pad. It should be noted that the present invention may also be utilized in other absorbent articles, such as diapers, adult incontinent products and the like. As used herein, the term "disposable absorbent article" includes articles for absorbing and retaining liquids, such as those discharged from the human body, and further, which articles are intended to be discarded after a single use. A "catamenial pad" is an absorbent article worn by females externally to the urogenital region for absorbing and containing menstrual fluids and other vaginal discharges.

Figure 1:
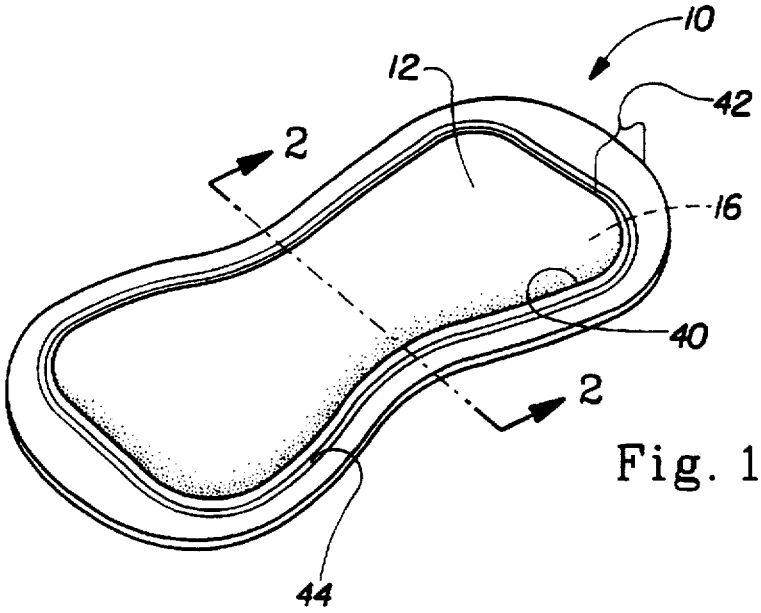
FIG. 1 is a perspective view of a disposable absorbent article incorporating the novel principles of the present invention.

A perspective view of a catamenial pad incorporating the anti-wicking seal of the present invention is depicted in FIG. 1. As best seen from FIG. 2, catamenial pad 10 is constructed of a first liquid permeable topsheet layer 12, a second liquid permeable topsheet layer 14, an absorbent core 16, and a liquid impermeable backsheet 18. First and second topsheet layers 12 and 14 may be either formed as separate sheets or as multiple plies of one composite material. Absorbent core 16 may be formed of a variety of absorbent materials, and preferably includes a predetermined amount of "Absorbent Gelling Material" particles 19, commonly referred to as AGM in the art. Absorbent core 16 should be flexible, compressible, and comfortable to the wearer. Moreover, the absorbent capacity of the material used in absorbent core 16 must be sufficient to absorb and retain the expected liquid loading on catamenial pad 10. In addition, the shape and dimensions of absorbent core 16 are selected to comfortably fit the urogenital region of the female wearer. FIG. 1 shows a generally hour-glass shaped absorbent core 16 that provides satisfactory fit and protection.

Liquid impermeable backsheet 18 prevents liquid which has penetrated first topsheet layer 12 and second topsheet layer 14 and has been absorbed by absorbent core 16 from soiling the undergarments of the wearer of catamenial pad 10. Backsheet 18 is preferably formed of a hydrophobic polyethylene film having a thickness approximately within the range of 0.010 to 0.050 millimeters, although other flexible, liquid impermeable materials may be used. The term "hydrophobic" is used herein to refer to a surface which is not wetted by contact with a liquid. The wetting of materials is generally defined in terms of contact angle and surface tension. These properties are discussed further in the publication of the American Chemical Society entitled "Contact Angle, Wettability, and Adhesion", edited by Robert F. Gould, copyright 1964, which is hereby incorporated by reference.

First topsheet layer 12 is liquid permeable and contacts the skin of the wearer of catamenial pad 10. It should therefore preferably be compliant, soft, and non-irritating to the skin of the wearer. First topsheet layer 12 is preferably formed of polyethylene film that is treated with a surfactant to enhance liquid penetration. The term "hydrophilic" is used herein to refer to a surface which is wetted by contact with a liquid. First topsheet layer 12 preferably has a multiplicity of transversely extending capillaries for encouraging liquid to rapid penetrate or strike through first topsheet layer 12 for subsequent absorption and retention by absorbent core 16.

Second topsheet layer 14 is preferably formed of polypropylene which is initially hydrophobic and has been treated with wetting agents to become hydrophilic. Second topsheet layer 14 is disposed between first topsheet layer 12 and absorbent core 16 for the purposes of resisting passage and escape of the AGM particles, which would cause a variety of problems.

When in use, catamenial pad 10 is preferably held in place by an undergarment (not shown). A band of adhesive 20 is affixed to a lower or outer surface 22 of backsheet 18 for adhering to the undergarment (not shown) to resist movement of catamenial pad 10 out of proper alignment with the urogenital region of the female wearer's body. A cover strip 24 may be initially provided for covering and protecting adhesive band 20, which is removed before use.

Figure 2:
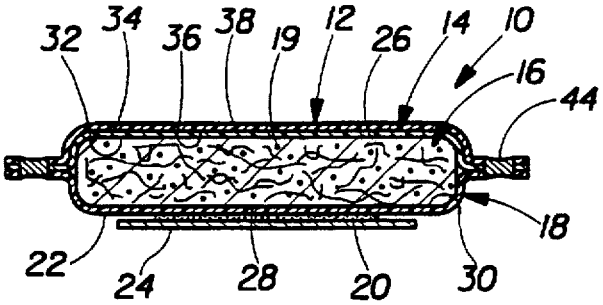
FIG. 2 is a cross-sectional view taken along line 2—2 of FIG. 1.

As best seen from FIG. 2, absorbent core 16 has a lower surface 28 and an upper surface 26 and which are respectively disposed adjacent to and contiguous with an upper surface 30 of backsheet 18 and a lower surface 32 of second topsheet layer 14. Moreover, second topsheet layer 14 has an upper surface 34 which is positioned adjacent to and contiguous with a lower surface 36 of first topsheet layer 12. Finally, first topsheet layer 12 has an upper surface 38 which is placed against the user's body when catamenial pad 10 is worn.

The lateral edges of absorbent core 16 define a perimeter 40. First and second topsheet layers 12 and 14 and backsheet 18 are formed generally without macroscopic perforations, and each have a shape similar to but larger than absorbent core 16. Thus, each of first and second topsheet layers 12 and 14, respectively, and backsheet 18 have a portion which extends outwardly from the perimeter of absorbent core 16 to define a continuous border segment which encircles absorbent core 16. Border segment 42 is generally relatively narrow, and may extend a distance of approximately 0.25 to 5 millimeters and preferably is approximately 3 millimeters wide. However, the width of border 42 may be uniform or vary about the perimeter of pad 10. Moreover, border segment 42 is relatively thin and flexible and is intended to provide improved protection against soiling of the vicinity surrounding the discharge region, as well as retain AGM particles within the absorbent article.

In accordance with the present invention, a liquid impermeable seal 44 is provided in border segment 42 which surrounds perimeter 40. Thus, seal 44 is adapted to prevent lateral migration (i.e., "wicking") of liquid from perimeter 40 of absorbent core 16, or first and second topsheet layers 12 and 14, through border segment 42 toward the peripheral edges of catamenial pad 10, thereby inhibiting premature side soiling of the wearer's undergarments. As a result, first topsheet layer 12, second topsheet layer 14 and backsheet 18 tend to remain relatively free of liquids, regardless of the amount of liquid contained in absorbent core 16. Liquid impermeable seal 44 is preferably disposed laterally inwardly as close as possible to perimeter 40 so that a greater portion of border segment 42 remains dry and unsoiled. Seal 44, in its preferred application, completely surrounds perimeter 40 without any gaps which would allow wicking and fluid leakage. In this most preferred application, the improved seal 44 of the present invention is specifically directed to inhibiting wicking of fluid through liquid permeable second topsheet layer 14 which is sandwiched between first topsheet layer 12 and backsheet 18 in border segment 42.

Figure 3:
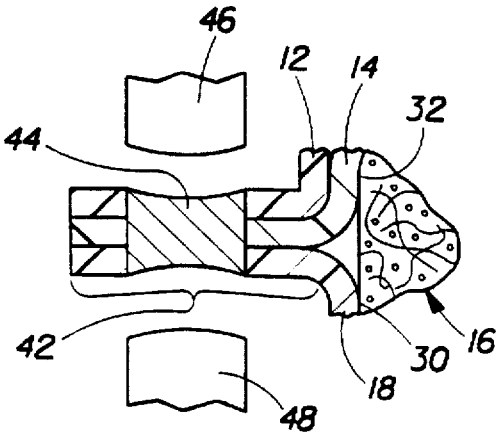
FIG. 3 is an enlarged view of a lateral edge of the absorbent article shown in FIG. 2 also showing an upper and lower crimp tool.

Seal 44 is preferably formed by the simultaneous application of pressure, with or without heat, commonly referred to as a "crimping" operation. Referring to FIG. 3, an upper and lower crimp tool 46 and 48 are shown for concurrently compressing first and second topsheet layers 12 and 14 and backsheet 18. Tools 46 and 48 should be wide enough so as not to cut, mar or tear first topsheet layer 12 or backsheet 18. During the "crimping" process, sufficient pressure, possibly with heat, is transferred via crimping tools 46 and 48 to melt first topsheet layer 12 and backsheet 18, thereby forming a solid yet flexible liquid impermeable seal 44. Thus, the pressure crushes second topsheet layer 14 to at least partially fill the remaining capillary spaces therein. First topsheet layer 12 and backsheet 18 melt around the material of second topsheet layer 14 creating a barrier for inhibiting wicking therethrough. The portions of the border outside of seal 44 are crimped with discrete spaced-apart bonds. This discrete bonding creates a reverse or negative capillary gradient, whereby any liquids inadvertently passing through seal 44 will tend to be attracted toward the more dense material in the seal 44 area, so any liquid movement outside seal 44 occurs along seal 44, as opposed to toward outer edge of border 42.

In an alternative embodiment of the present invention, second topsheet layer 14 is formed of hydrophilic non-woven or apertured polyethylene film having a lower melting temperature than first topsheet layer 12 and backsheet 18. Upon the application of localized pressure, during the "crimping" process, with or without heat, polyethylene second topsheet layer 14 will melt before first topsheet layer 12 and backsheet 18 and will propagate and mingle with the material of first topsheet layer 12 and backsheet 18, thus forming a liquid impermeable seal 44 which appears similar on a macroscopic level to the seal formed by the first preferred embodiment of the present invention, in which first topsheet layer 12 and backsheet 18 melt prior to second topsheet layer 14. The crimping process may be varied to cause first and second topsheet layers 12 and 14, as well as backsheet 18, to melt to form seal 44.

Figure 4:
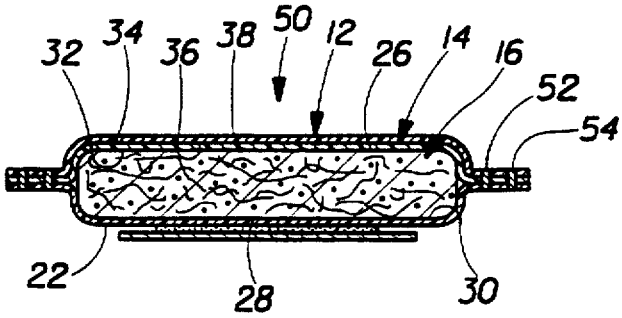
FIG. 4 is a cross-sectional view of an alternative embodiment of the present invention.
Figure 5:
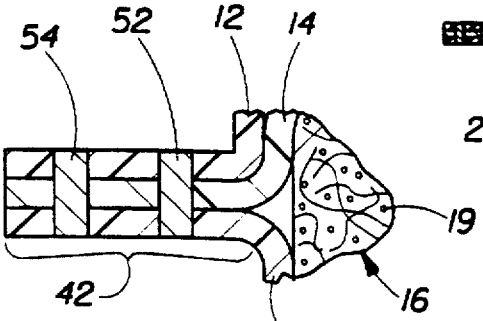
FIG. 5 is an enlarged view of a lateral edge of the absorbent article shown in FIG. 4.

A second alternative embodiment of the present invention is shown in FIGS. 4 and 5, which depict a catamenial pad 50 generally similar to catamenial pad 10 of FIGS. 1 through 3. For purposes of clarity, like reference numerals are used to designate those elements of catamenial pad 50 that are similar to, or identical with, the above-noted elements of catamenial pad 10. Pad 50 has a first or inner liquid impermeable seal 52 which is disposed as close as possible to perimeter 40 of absorbent core 16 and surrounds perimeter 40. In addition, catamenial pad 50 is also provided with a second or outer seal 54 for providing additional resistance against wicking of liquid that enters border segment 42 beyond first seal 52. The present invention contemplates the possibility of using three or even more seals. As with the preferred embodiments shown in FIGS. 1 through 3, second topsheet layer 12 may be formed preferably of hydrophobic polypropylene which is treated with wetting agents to become hydrophilic, or alternatively can be formed of hydrophilic non-woven or apertured polyethylene. Accordingly, first and second seals 52 and 54 will be formed by the melting of first topsheet layer 12 and backsheet 18 with the preferred selection of polypropylene for second topsheet layer 14, or in the alternative, seals 52 and 54 will be formed by the melting of second topsheet layer 14 in the case of selection of hydrophilic polyethylene for second topsheet layer 14.

Figure 6:
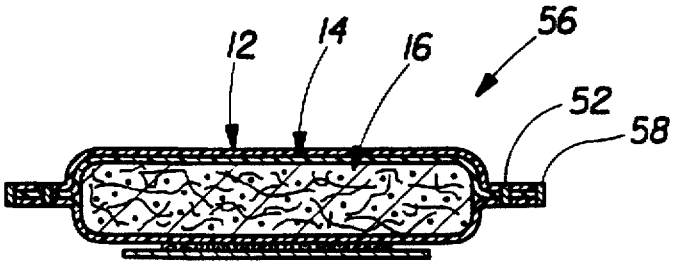
FIG. 6 is a cross-sectional view of another alternative embodiment of the present invention.
Figure 7:
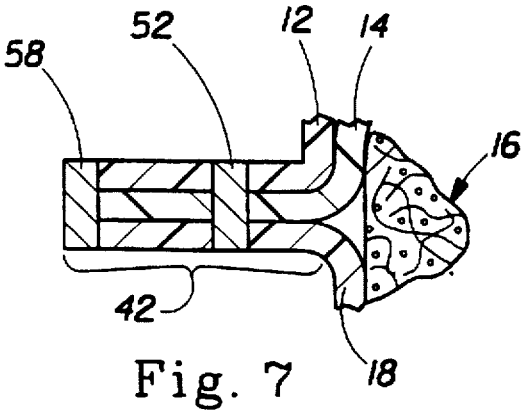
FIG. 7 is an enlarged view of a lateral edge of the absorbent article shown in FIG. 6.

Another alternative embodiment of the present invention is depicted in FIGS. 6 and 7, in which a catamenial pad 56 is constructed substantially similar to catamenial pad 50 shown in FIGS. 4 and 5, and includes a first or inner seal 52 and a second or outer seal 58. In this embodiment, outer seal 58 is disposed at the laterally outermost edge of border segment 42 defined by first and second topsheet layers 12 and 14, as well as backsheet 18. The alternative embodiments of the present invention provide for selectively positioning various liquid impervious seals in order to maximize their effectiveness while maintaining comfort and preventing irritation to the wearer.

Figure 8:
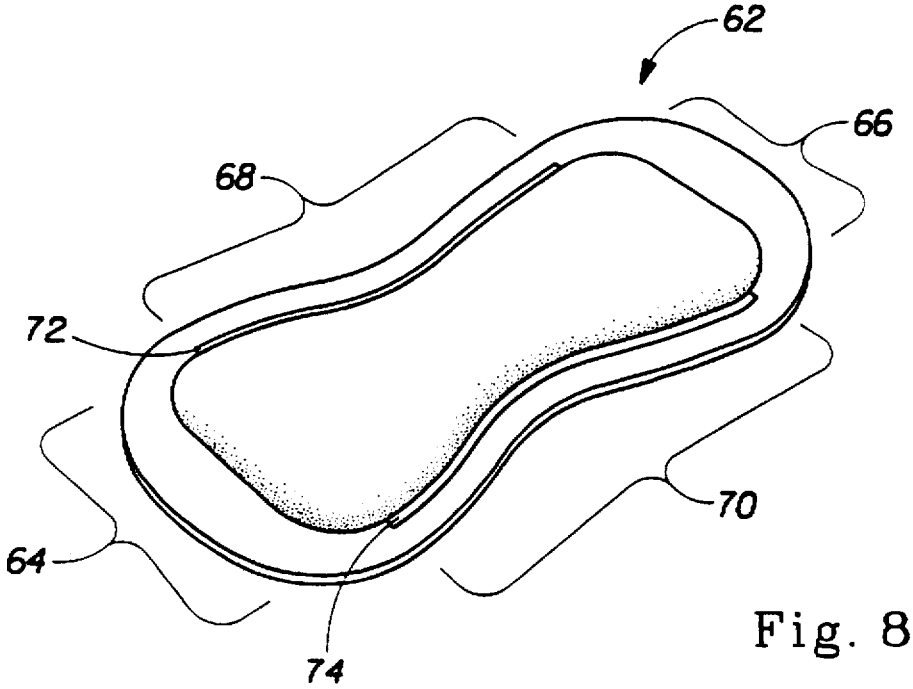
FIG. 8 is a perspective view of a disposable absorbent article arranged according to an alternative embodiment of the present invention.

Yet another alternative embodiment of the present invention is depicted in FIG. 8. Catamenial pad 62 is formed generally similar to pad 10, and has an anterior portion 64, posterior portion 66, and first and second sides edges 68 and 70. Liquid impermeable seals 72 and 74 are similar to seal 44, but extend only along side edges 68 and 70. It has been found that seals 68 and 70 may be more easily manufactured than seal 44, which completely surrounds core 16.

It should be understood that an unlimited number of configurations of the present invention can be realized. The foregoing discussion discloses and describes merely exemplary embodiments of the present invention. One skilled in the art will readily recognize from the discussion and from the accompanying drawings and claims that various changes and modifications can be made without departing from the spirit and scope of the invention, as defined in the following claims.

What is claimed is:

1. An absorbent article for absorbing liquids, comprising:

a first liquid permeable topsheet layer;

a second liquid permeable topsheet layer;

a liquid impermeable backsheet;

an absorbent core disposed between said backsheet and said second topsheet layer, said second topsheet layer being disposed between said absorbent core and said first topsheet layer, and wherein said first topsheet layer, said second topsheet layer and said backsheet each extend laterally beyond the perimeter of said absorbent core to define a continuous border segment surrounding said absorbent core; and a liquid impermeable seal formed in said border segment and surrounding at least a portion of said perimeter of said absorbent core, said seal extending from an outer surface of said first topsheet layer to an outer surface of said backsheet, such that said seal is adapted to prevent migration of liquid from said absorbent core laterally outward beyond said seal.

* * * * *